United States Patent [19]

Topfmeier et al.

[11] Patent Number: 4,822,807

[45] Date of Patent: Apr. 18, 1989

[54] PHARMACEUTICAL COMPOSITION CONTAINING A STABLE MODIFICATION OF TORASEMIDE

[75] Inventors: Fritz Topfmeier, Heidelberg; Gustav Lettenbauer, Lampertheim, both of Fed. Rep. of Germany

[73] Assignee: Boehringer Mannheim GmbH, Mannheim, Fed. Rep. of Germany

[21] Appl. No.: 111,439

[22] Filed: Oct. 20, 1987

Related U.S. Application Data

[62] Division of Ser. No. 895,355, Aug. 11, 1986, Pat. No. 4,743,693.

[30] Foreign Application Priority Data

Aug. 17, 1985 [DE] Fed. Rep. of Germany ....... 3529529

[51] Int. Cl.$^4$ ................. C07D 213/74; C07D 213/75; A61K 31/44
[52] U.S. Cl. .................................. 514/347; 514/346; 546/291; 546/294
[58] Field of Search ................ 546/294, 291; 514/346, 514/347

[56] References Cited

U.S. PATENT DOCUMENTS

Re. 30,633  4/1977  DeLarge et al. ............... 514/332
4,018,929  4/1977  DeLarge et al. ............... 514/335

FOREIGN PATENT DOCUMENTS

0003383  8/1979  European Pat. Off. ............ 514/332

OTHER PUBLICATIONS

Chem. Abstracts, vol. 92(15), abst. no. 128,739e, Apr. 14, 1980.
Chem. Abstracts, vol. 95(25), abst. no. 214,829n, Dec. 21, 1981.
Chem. Abstracts, vol. 97(21), abst. no. 174,700w, Nov. 22, 1982.
REMINGTONS' PHARMACEUTICAL SCIENCES, Fourteenth Edition, pp. 140–142, 170, 208–221, Mack Publishing Co., (1970).
Dupont et al., "Structure Cristalline et Moléculaire dûn Divrétigue . . . ", Acta Cryst. B34, 1304–1310, (1978).
Dupont et al., "Structure dûne Seconde Variété de la Torasémide", Acta Cryst. B34, 2659–2662, (1978).

Primary Examiner—Alan L. Rotman
Attorney, Agent, or Firm—Felfe & Lynch

[57] ABSTRACT

The present invention provides a process for the preparation of cystalline torasemide in the pure modification I (monoclinic, space group P2$_1$/c, melting point 162° C.) from torasemide of modification II (monoclinic, space group P2/n, melting point 169° C.), wherein a suspension of torasemide of modification II is stirred in water with the addition of a catalytic amount of modification I until the rearrangement is complete.

The present invention also provides pharmaceutical compositions containing torasemide of modification I.

3 Claims, No Drawings

PHARMACEUTICAL COMPOSITION CONTAINING A STABLE MODIFICATION OF TORASEMIDE

This is a Divisional of Ser. No. 895,355, filed Aug. 11, 1986 now U.S. Pat. No. 4,243,693.

The present invention is concerned with a process for the preparation of a stable modification of torasemide.

Torasemide (1-isopropyl-3-[(4-m-toluidino-3-pyridyl)-sulphonyl]-urea) is a compound with interesting pharmacological properties which is described in Example 71 of U.S. Pat. No. Re 30,633 as 3-isopropylcarbamyl sulfonamido-4-(3'-methyl)-phenylaminopyridine. In particular, this compound has a strong diuretic action in the case of which water and sodium ions are excreted relatively more strongly than potassium ions. The compound is, therefore, of great interest as a diuretic agent.

In the preparation of this compound, a purification is normally included in which the compound in question is dissolved in an aqueous or aqueous alcoholic solution of sodium hydrogen carbonate and, after filtering off from impurities, the torasemide is again precipitated out with acetic acid or carbon dioxide. In the case of this process, the product is obtained in the form of white crystals with a melting point of 163°–164°C.

From Acta Cryst., 1978, pp. 2659–2662 and Acta Cryst., 1978, pp. 1304–1310, it is known that torasemide can occur in two modifications which differ X-ray crystallographically. Both modifications are simultaneously present when a solution of torasemide in petroleum ether/ethanol is slowly evaporated. The crystals, which are characterised not only as prisms with a melting point of 169° C. but also as leaflets with a melting point of 162° C., are, however, only described in these literature references with regard to their X-ray crystallographic properties. The modification with the melting point of 169° C., which is hereinafter referred to as modification I, crystallises monoclinically in the space group $P2_1/c$, and the modification with the melting point of 162° C., which is hereinafter referred to as modification II, crystallises monoclinically in the space group $P2/n$.

The modification obtained in the case of the preparation and normal purification by precipitating the torasemide with carbon dioxide is modification II which usually also results in the case of recrystallisations from other solvents. Since this form, in the case of storage of the pure active material, does not change and, in the case of all purification experiments, forms the predominant form, it was assumed that this modification II is also stable. Surprisingly, we have now ascertained that torasemide of modification II, when it is present in very finely divided form in pharmaceutical tablets, rearranges more or less quickly into modification I, whereby the crystal size and speed of dissolving of the active material upon introducing the tablets into water can be significantly changed. Since, on the other hand, as is known, the speed of dissolving represents one of the important characteristics of a pharmaceutical form of administration and thus, in order to be able to dose reproducibly, must not differ from one tablet to another, the problem exists of finding a form of administration of torasemide which does not change its speed of dissolving during storage. Since the uncontrollable change of the speed of dissolving depends upon the rearrangement of modification II into modification I of the torasemide, it was obvious ab initio to use modification I from which, from our investigations, it followed that it is also stable in tablets and did not rearrange again back into modification II.

Therefore, the present invention provides oral forms of administration which contain torasemide of modification I as active material.

The process, which is sufficient for X-ray crystallography, of allowing both modifications to crystallise out together from the same solvent mixture and to separate them according to their macroscopic crystal form is, of course, useless for a large-scale preparation since such a separation of the crystals would not be feasible. Furthermore, it was known that torasemide, upon heating in most solvents, cyclises irreversibly with the anilino nitrogen atom. Therefore, a recrystallisation from most solvents is not suitable for the preparation of modification I. Consequently, there was the further problem of finding a process for the preparation of the pure modification I of torasemide which can be carried out simply and economically and without decomposition of the torasemide.

Surprisingly, we have now found that torasemide of modification II can be rearranged into modification I when a suspension thereof in water is seeded with very finely divided crystal nuclei of modification I and this suspension is stirred until the whole amount thereof has undergone rearrangement into modification I.

At ambient temperature, this rearrangement takes place relatively slowly so that a period of 10 to 14 days is necessary. However, the suspension can also be heated to temperatures of 70° to 90° C., in which case the reaction proceeds to completion within 3 to 6 hours. Whereas in the case of heating torasemide in solvents such as ethanol, ethyl acetate, methylene chloride and chloroform, decomposition products are formed in considerable amounts, torasemide can, surprisingly, be heated in water for several days to 90° C. without noticeable decomposition. Furthermore, it was surprising that even the addition of small amounts (up to 1%) bring about a rearrangement since torasemide of modification I has, in any case, a solubility of 1.9 g./liter at 90° C. Purely on the basis of the solubility, it was to have been expected that these small amounts of torasemide would dissolve in the aqueous suspension medium.

Since the rearrangement itself proceeds even in pure water, this process has the further advantage that no additional impurities, such as solvents, catalytically-acting acids or bases, etc. are entrained into the product. On the contrary, due to the recrystallisation procedure, impurities present in the original modification II pass into the water.

Oral forms of administration containing torasemide of modification I are produced in the usual way with the use of pharmacologically acceptable adjuvants, for example sugar, starch, starch derivatives, cellulose, cellulose derivatives, mould separation agents and anti-adhesion agents, as well as possibly flow regulation agents. In particular, in the case of the use of torasemide of modification I, aqueous process steps, for example granulation, can be carried out.

For the desired quality-determining parameter of the form of administration according to the present invention, it is especially advantageous when the active material torasemide of modification I is used with the following particle size distribution:

at least 90% $\leq 96$ μm. and,
at least 50% $\leq 48$ μm.

In comparison with pharmaceutical formulations with the active material torasemide of modification II, the formulations according to the present invention have a rapid in vitro rate of dissolving which remains unchanged even after comparatively long storage at temperatures higher than ambient temperature and at a comparatively high atmospheric humidity.

The rapidly commencing pharmacological action of these compositions is ensured by the rapid rate of dissolving of the active material from the form of administration. Thus, for example, after 15 minutes more than 60% has gone into solution and after 30 minutes more than 80%, the test method used being the paddle test USP XXI.

The following Examples are given for the purpose of illustrating the present invention:

EXAMPLE 1.

10 kg. Torasemide, which has been prepared according to U.S. Pat. No. Re 30,633 and has been purified by reprecipitation from sodium bicarbonate solution with carbon dioxide, are suspended in the 10 fold amount of water and 100 g. of torasemide of modification I from a previous batch are added thereto. The suspension is heated to 90° C., stirred at this temperature for 6 hours, cooled to ambient temperature and again stirred for 30 minutes. Thereafter, the crystals are filtered off with suction, washed with 40 litres of water and dried in a vacuum drying cabinet at 50° C., 9.91 kg. of torasemide of modification I being obtained.

The X-ray diffraction diagram corresponds to that of the pure modification I and a testing for purity with HPLC corresponds to the pure starting material.

Crystal nuclei of modification I can possibly also be obtained according to the process described in Acta Cryst., 1978, p. 1304.

EXAMPLE 2.

900 g. Torasemide of modification II are suspended in 10 litres of water and stirred at ambient temperature in the presence of 10 g. torasemide of modification I. After 8 days, a sample no longer contains any trace of modification II. The product is filtered off and dried in a vacuum drying cabinet at 50° C., 875 g. of torasemide of modification I thereby being obtained. The purity corresponds to that of the starting material and the X-ray crystallographic spectrum corresponds to that of the pure modification I.

For comparison, the same batch but without the addition of modification I was stirred at ambient temperature for 10 days without a rearrangement into modification I taking place.

EXAMPLE 3.

10 kg. Crude torasemide, which has been prepared according to the procedure of U.S. Pat. No. Re 30,633, is suspended in 100 litres of water and mixed with 30 litres of 1N aqueous sodium hydroxide solution. After treatment with 500 g. of active charcoal and filtration, there is obtained a clear yellowish solution from which, by the addition of 1N sulphuric acid at ambient temperature up to the achievement of a pH value of 7.5, the torasemide is again precipitated out (consumption about 29 litres). 100 g. of torasemide of modification I are added to this suspension and the solution is heated for 6 hours to 90° C. During this time, the modification rearrangement takes place. The suspension is cooled to ambient temperature and the crystallisate is centrifuged off. The crystallisate is washed with 50 litres of water and finally dried at 50° C. in a vacuum drying cabinet, 9.82 g. of pure torasemide of modification I being obtained.

This Example shows that the rearrangement according to the present invention can also be carried out in the presence of foreign salts such as are present in the case of the normal precipitation of torasemide.

EXAMPLE 4.

Production of a 2.5 mg. tablet.

Torasemide of modification I is mixed in the usual way with lactose monohydrate and maize starch, granulated with water, dried and sieved (granulate 1). Highly dispersed silicon dioxide and magnesium stearate are mixed, sieved and admixed with granulate 1. This mixture is then tabletted in conventional manner. Production formulation for 100,000 tablets:

| | |
|---|---|
| torasemide | 0.25 kg. |
| lactose monohydrate | 6.05 kg. |
| maize starch | 1.60 kg. |
| silicon dioxide, highly dispersed | 60.00 g. |
| magnesium stearate | 40.00 g. |
| water, purified | 1.20 kg. |

EXAMPLE 5.

Production of a 100 mg. tablet.

Torasemide of modification I is mixed with lactose monohydrate, maize starch and a part of the magnesium stearate. The mixture is compacted and sieved to the desired gain size and grain size distribution (granulate 1). Highly dispersed silicon dioxide and magnesium stearate are mixed and sieved and admixed with granulate 1. The mixture is then tabletted in conventional manner.

Production formulation for 100,000 tablets:

| | |
|---|---|
| torasemide | 10.0 kg. |
| lactose monohydrate | 2.0 kg. |
| maize starch | 7.7 kg. |
| silicon dioxide, highly dispersed | 0.2 kg. |
| magnesium stearate | 0.1 kg. |

It will be understood that the specification and examples are illustrative but not limitative of the present invention and that other embodiments within the spirit and scope of the invention will suggest themselves to those skilled in the art.

What is claimed is:

1. A diuretic pharmaceutical composition comprising an effective amount of rapidly dissolving crystalline torasemide of pure modification I (monoclinic, space group P2$_1$/c, melting point 169° C.) substantially free of crystalline torasemide of modification II (monoclinic, space group P2/n, melting point 162° C.) and a pharmacologically acceptable carrier, said torasemide of modification I having solubility characteristics such that at least 60% is dissolved in water after 15 minutes, and at least 80% is dissolved in water after 30 minutes.

2. The composition of claim 1 comprising, by weight, approximately:
   100 parts of the torasemide of modification I and, as the carrier,
   20 parts lactose monohydrate,
   77 parts maize starch, 2 parts silicon dioxide and, 1 part magnesium stearate.

3. The composition of claim 1 comprising, by weight, approximately:

25 parts of the torasemide of modification I and, as the carrier,
605 parts lactose monohydrate,
160 parts maize starch,
6 parts silicon dioxide and
4 parts magnesium stearate.

* * * * *